(12) United States Patent
Brandt et al.

(10) Patent No.: US 7,447,644 B2
(45) Date of Patent: Nov. 4, 2008

(54) SYSTEM AND USER INTERFACE FOR PROCESSING HEALTHCARE RELATED EVENT INFORMATION

(75) Inventors: Samuel I. Brandt, Malvern, PA (US); Jan DeHaan, Downington, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1160 days.

(21) Appl. No.: 10/052,192

(22) Filed: Jan. 17, 2002

(65) Prior Publication Data
US 2003/0050797 A1 Mar. 13, 2003

Related U.S. Application Data

(60) Provisional application No. 60/318,664, filed on Sep. 12, 2001.

(51) Int. Cl.
*G06Q 10/00* (2006.01)
(52) U.S. Cl. .................. 705/2; 705/3; 705/8; 705/9
(58) Field of Classification Search ............ 705/2, 705/3, 8, 9; 600/300
See application file for complete search history.

(56) References Cited

U.S. PATENT DOCUMENTS

| | | | |
|---|---|---|---|
| 5,077,666 A | 12/1991 | Brimm et al. | |
| 5,319,543 A | 6/1994 | Wilhelm | |
| 5,692,125 A | 11/1997 | Schloss et al. | |
| 5,826,239 A | 10/1998 | Du et al. | 705/8 |
| 5,918,226 A | 6/1999 | Tarumi et al. | 707/10 |
| 6,024,699 A | 2/2000 | Surwit et al. | |
| 6,037,940 A | 3/2000 | Schroeder et al. | 345/348 |
| 6,073,109 A * | 6/2000 | Flores et al. | 705/8 |
| 6,078,982 A * | 6/2000 | Du et al. | 710/200 |
| 6,151,583 A | 11/2000 | Ohmura et al. | 705/8 |
| 6,278,977 B1 | 8/2001 | Agrawal et al. | 705/7 |

(Continued)

FOREIGN PATENT DOCUMENTS

EP    0 950 971 A2    10/1999

OTHER PUBLICATIONS

Cugola, G. et al. "Exploiting an event based infrastructure to develop complex distributed systems," IEEE (1998) pp. 261-270.

*Primary Examiner*—C Luke Gilligan
*Assistant Examiner*—Michelle Le
(74) *Attorney, Agent, or Firm*—Alexander J. Burke

(57) ABSTRACT

A system for scheduling a set of tasks to be performed by at least one individual to support healthcare delivery employs a method for providing a user interface for processing an event. The event represents a change in circumstances potentially affecting healthcare delivered to a patient. The method involves initiating generation of at least one display image in response to user command. The display image or images support the identification of an event and an associated parameter as well as the designation of a predetermined process associated with the identified event. The display image or images also support user indication of the parameter to be provided to the predetermined process in response to occurrence of the event. The predetermined process comprises a set of tasks to be performed by at least one individual to support healthcare delivery. The display image or images also support designating an executable procedure to be initiated in response to occurrence of the identified event.

20 Claims, 7 Drawing Sheets

U.S. PATENT DOCUMENTS

| | | | |
|---|---|---|---|
| 6,279,042 B1 | 8/2001 | Ouchi | 709/240 |
| 6,282,531 B1 | 8/2001 | Haughton et al. | 706/50 |
| 6,458,080 B1 * | 10/2002 | Brown et al. | 600/300 |
| 7,051,071 B2 * | 5/2006 | Stewart et al. | 709/204 |
| 2002/0062230 A1 * | 5/2002 | Morag et al. | 705/3 |
| 2003/0050821 A1 | 3/2003 | Brandt et al. | |
| 2004/0122701 A1 * | 6/2004 | Dahlin et al. | 705/2 |

* cited by examiner

SYSTEM AND USER INTERFACE FOR PROCESSING HEALTHCARE RELATED EVENT INFORMATION

This is a non-provisional application of provisional application Ser. No. 60/318,664 by S. Brandt et al. filed Sep. 12, 2001.

This application is co-pending with commonly owned related application, Ser. No. 10/051,664 filed Jan. 17, 2002.

FIELD OF THE INVENTION

This invention concerns a system and user interface supporting scheduling a workflow process comprising a set of tasks to be performed by at least one individual to support healthcare delivery.

BACKGROUND OF THE INVENTION

Modern healthcare requires the concurrent provision of services by many health-care workers to many patients. In order to accomplish this, healthcare delivery has been organized into specialized departments such as nursing, laboratory, and radiology departments. Each department has responsibility for accomplishing its particular, often specialized, subset of tasks. Unfortunately, this has resulted in fragmented patient care and sub-optimal healthcare operations. A single healthcare process such as the ordering and administration of a medication, requires the participation of many health-care workers, possibly across many departments, and is therefore fraught with opportunities for error and delay.

Clinical and healthcare information systems provide a computerized interface for health-care workers to perform individual tasks. However, these systems typically have limited capability to manage the sequence of tasks involved in healthcare processes. This is particularly true when the processes require the involvement of multiple health-care workers. Workflow management systems are designed to manage complex processes that include individual work steps performed by multiple workers and systems. They allow the customized configuration of these processes, as well as continuous monitoring and management while the processes are in progress. In order to optimally employ a workflow management system in healthcare, it is desirable that the system support configuration of a workflow (i.e. determination of a sequence and schedule of tasks to be performed by one or more individuals) at a local level. Such a local level may be within a facility where the workflow is to be implemented, for example.

Existing healthcare or clinical information systems provide user interfaces for performing individual healthcare tasks and viewing and recording of information. This includes, for example, results reporting, goods and services ordering, clinical and nursing care documentation, and financial or operational data capture. However, existing systems are typically task oriented, and provide interfaces for individuals to accomplish specific tasks. As such they fail to provide the flexible and comprehensive user interfaces and systems needed to support the adequate management of clinical care and documentation processes that involve multiple users, and which occur over an extended period of time, and are amenable to reengineering. A system according to invention principles addresses these deficiencies and derivative deficiencies. Specifically the disclosed system supports creation, initiation and modification of workflow processes that sequence tasks to be performed by healthcare personnel and also supports the monitoring and management of the tasks and of their progress until their successful completion.

SUMMARY OF INVENTION

A system and user interface integrates and processes event associated messages affecting healthcare delivered to a patient and supports creation, initiation and modification of currently operating workflow processes involving processing of event messages. A system for scheduling a set of tasks to be performed by at least one individual to support healthcare delivery employs a method for providing a user interface for processing an event. The event represents a change in circumstances potentially affecting healthcare delivered to a patient. The method involves initiating generation of at least one display image in response to user command. The display image or images support the identification of an event and an associated parameter as well as the designation of a predetermined process associated with the identified event. The display image or images also support user indication of the parameter to be provided to the predetermined process in response to occurrence of the event. The predetermined process comprises a set of tasks to be performed by at least one individual to support healthcare delivery.

DETAILED DESCRIPTION OF THE DRAWING

Figure 1:
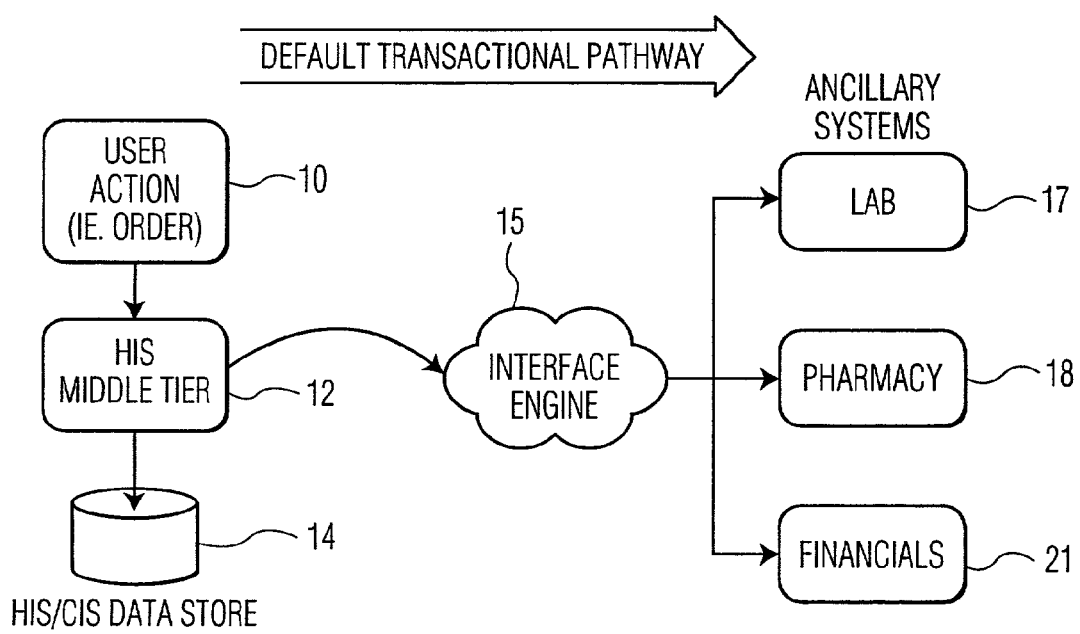
FIG. 1 shows an existing healthcare or clinical information system for invoking actions in external systems.

FIG. 1 shows an existing healthcare or clinical information system for invoking actions in external systems. In such a system, messages identifying events or actions taken in a Healthcare Information System (HIS) 12 (perhaps involving storage unit 14) in response to user actions 10, are communicated to external systems 17-21 through an interface engine 15. An event as used herein is an action or occurrence representing a change in circumstances potentially affecting healthcare delivered to a patient. An event message identifying such an event may be generated due to action by healthcare personnel, by an operating process (perhaps for influencing other operating processes), by a non-healthcare system such as an administrative application (perhaps involving financial transaction information), or by patient monitoring equipment. An event message may also be generated by other devices for example: patient locator or proximity devices, and medical equipment such as IV pumps. Interface engine 15 may comprise a workflow processing application or other application supporting communication with external systems 17-21. A workflow as used herein comprises a sequence of tasks or operations that are scheduled for performance, or are being performed, by one or more entities including individuals, groups of individuals, or personnel assigned to perform particular functions or roles. External systems 17-21 comprise a laboratory 17, pharmacy 18 and financial application (such as for patient service tracking and billing) 21, for example, but may also encompass a broader range of systems including any system with which HIS 12 performs a transaction or data exchange. Further Healthcare Information System (HIS) 12 may comprise other types of information system such as a Clinical Information System or Critical Care Information System or another Information system. Further, in other embodiments HIS 12 may include non-healthcare information systems such as financial information systems provided that such a system involves performing a sequence of tasks that is susceptible to modification as a result of occurrence of an event.

The existing systems workflow processing function exemplified in the unit 15 function of FIG. 1 has a number of deficiencies. These include limited flexibility in configuring workflow processes and limited capability for creating workflow processes that may be dynamically re-configured in response to events. Existing workflow management systems are typically limited in the flexibility they allow in configuring workflow processes and in allocating codes for identifying processes and events, for example. This is insufficient for healthcare applications in which a healthcare enterprise HIS system supplied by one vendor is oblivious of workflow process configurations implemented using workflow management application software provided by a different vendor. In addition, existing workflow management systems typically assume that individual work processes are autonomous and are unaffected by other running processes. In contrast, real healthcare processes constantly affect each other. For example, a patient being taken to radiology for a diagnostic study interferes with the administration of intravenous medication in the patient's room. Further, the complexity of modern healthcare enterprises means that a healthcare workflow process may need to be responsive to multiple different healthcare events, and also that a single event may impact multiple different concurrently operating healthcare processes. For example, an order to discharge a patient from a hospital may have multiple workflow processes associated with it, such as management of discharge medications, cancellation of dietary orders, and initialization of a discharge billing process. Further, a single workflow management process to cancel and to re-issue dietary orders may occur as a consequence of a discharge order, an order of "NPO" or nothing by mouth, or the transfer of a patient to surgery, for example. This implies a more sophisticated mechanism is required for invoking workflow processes than existing workflow management systems currently support. The disclosed system supports creation and configuration of healthcare processes that interact with each other and respond to changes and events originating in other processes.

The disclosed system and user interface integrates and processes event associated messages affecting healthcare delivered to a patient. The system provides a means for ensuring that messages are generated upon occurrence of selected events and for forwarding those generated messages to a workflow management system. The system also provides a method and user interface for linking a configured workflow process to a healthcare event so that a selected workflow process adapts upon occurrence of the event. For this purpose the system advantageously categorizes and filters events generated by an HIS to ensure that the events affecting the configured workflow process, or other healthcare workflow processes, are forwarded to the workflow management system. The filter thereby excludes a potentially large volume of event items of no consequence to system workflow processes. This significantly reduces the workload involved. Upon occurrence and detection of a user selected particular event, the system further allows a user to predetermine which one of multiple different workflow processes is implemented. Thereby, at user discretion, occurrence of an event may result in a default workflow process or another different workflow process being implemented. Further, the selected workflow process may also be further adapted upon occurrence of additional events. This enables conventional workflow processes to be employed as default processes or allows dynamically adaptive workflow processes to be implemented or allows both types of process to operate in parallel. This supports flexible workflow management and enables a considerable degree of flexibility in workflow process implementation and re-engineering upon healthcare system alteration or modification.

Figure 2:
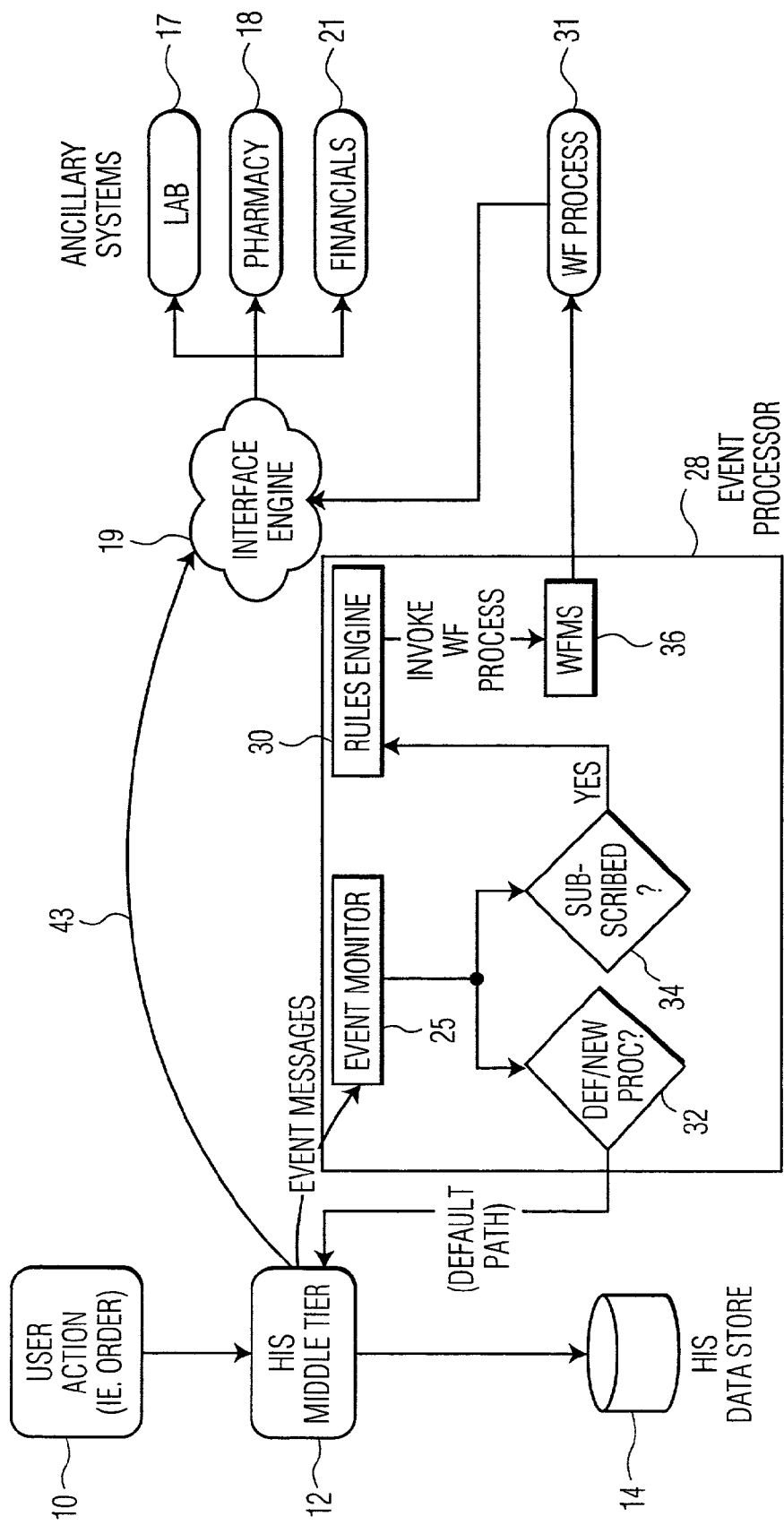
FIG. 2 shows a system that allows healthcare enterprises to create and configure workflow processes (comprising task sequences to be performed) responsive to events generated from a Healthcare Information System (HIS), according to invention principles.

FIG. 2 shows a system that allows healthcare enterprises to create and configure workflow processes (comprising task sequences to be performed) and to link the created workflow processes to events generated from HIS 12. In response to user actions 10, HIS 12 using storage 14 generates event messages and communicates them to event monitor 25 (in event processor 28). The event messages include event identifiers and metadata that identify user actions and other occurrences associated with healthcare delivery and support that take place in a healthcare enterprise and potentially affect healthcare delivered to a patient. Event messages provided by HIS 12 may identify user orders, documentation, and reports. Examples include such items as: a physician order for "Gentamicin 120 mg IV Stat then 80 mg every 8 hours", a nursing documentation of "2 cm area of redness on the patient's left lateral heel", or a microbiology report of "methacillin resistant staph aureus" cultured from a skin lesion of a newborn in the level one nursery. Such orders and observations require action by healthcare personnel and are advantageously processed by the FIG. 2 system.

In a conventional system a Gentamicin order, for example, is simply encoded in Health Level 7 (HL 7) format and forwarded to a pharmacy system for preparation of the drug. In contrast, the system of FIG. 2 creates and manages a workflow that accommodates the healthcare implications and consequences of such an order. The order intends a sequence of at least 7 events, for example, including the mixing of the medication, its transport to the patient's room, the insertion of an IV line if required, the infusion of the drug, nursing oversight to ensure that the drug infuses properly, nursing documentation of the infusion, and adjustment of subsequent doses to maintain the appropriate interval. In the case of receiving nursing documentation or a microbiology report event messages, the FIG. 2 system implements a consistent set of workflow processes for responding to the nurse observations and the outcome of the microbiology test. In the first case, the FIG. 2 system initiates a process including a scheduled task to protect the patient from skin breakdown and in the second case, the FIG. 2 system initiates a process including a scheduled task to implement an isolation procedure within a nursery.

The event messages also include parameter values and other metadata that is to be provided to a particular workflow process application in response to occurrence of a corresponding particular event. In the case of a drug order event, for example, the parameters may include a patient identifier, a drug identifier, drug strength, method of administering the drug, and dosing information. In the case of a nursing documentation of skin findings report event, the parameters may include a patient identifier, a finding identifier, descriptors, and site identifiers. Event monitor 25 categorizes and filters the received event messages and forwards those messages that are associated with registered workflow processes. Other event messages that are not associated with registered workflow processes are excluded. For this purpose event monitor 25 maintains a database including a map associating events, event identifiers and parameter identifiers with workflow processes. The map is used in determining parameter values and other data that is to be provided to a particular workflow process application in response to occurrence of a corresponding particular event.

In response to receiving an event message, event monitor 25 examines its map to determine whether a workflow process is associated with the event identified by the event identifier in the received message. If the identified event is associated with a particular workflow process (decision 34 of FIG. 2), event monitor 25 examines any parameters associated with the identified event and conveyed in the received event message from HIS 12. Specifically, monitor 25 determines if received event parameter values match predetermined criteria associated with the corresponding event. The predetermined criteria are specified during an event registration process during which a workflow process is associated with one or more identified events and associated event parameters. Thereby a workflow process is associated with one or more events and related event parameter values. If event monitor 25, using its map, finds that no workflow process is associated with the identified event (decision 32 of FIG. 2), it disregards the event message and returns a message to HIS 12 instructing HIS 12 to proceed with default processing. Such default processing may involve HIS 12 communicating via messages 43 with external systems 17-21 through an interface engine 19 in support of a default workflow process in similar fashion to that described in connection with FIG. 1, for example.

Event monitor 25 performs further operations if it determines in decision 34 that the identified event is associated with a particular workflow process and the received event parameter values are within a predetermined range. Specifically, monitor 25 determines from predetermined user selection information whether a default process is to be replaced by a workflow managed process that is invoked as a consequence of the event. If it is not to be replaced, monitor 25 returns a message to HIS 12 instructing HIS 12 to proceed with the default workflow processing. If it is to be replaced HIS 12 surrenders processing to event monitor 25 and the particular workflow process associated with the identified event by the monitor 25 internal map is implemented. Further, event monitor 25 provides rules engine 30 with the event identifier and associated event parameter values for use in implementing the particular workflow process.

In addition, monitor 25 also determines from predetermined user selection information whether there is an executable procedure (e.g. a script file) associated with the particular workflow process. Such a procedure may incorporate logic determining how an event associated workflow process is initiated or processed, for example. If there is such an associated procedure, monitor 25 also provides the procedure to rules engine 30 for execution. Alternatively the procedure may be pre-stored in rules engine 30, in which case monitor 25 commands engine 30 to initiate execution of the procedure. Rules engine 30 uses the information and commands received from monitor 25 to call the Workflow Management System 36 and instruct it to implement the event associated particular workflow process 31. It does this by creating and initiating a copy (an instance) of the desired event associated particular workflow process. In a complex system a workflow process may be implemented multiple times (i.e. as multiple instances) for different patients, for example. Therefore, process copies are made of a template process and the copies (instances) are the processes that are actually implemented. The multiple workflow process instances may or may not be in concurrent operation. The implemented workflow process may also be configured to communicate with users and other systems (e.g. laboratory 17, pharmacy 18 and financial system 21) via interface engine 19.

Figure 3:
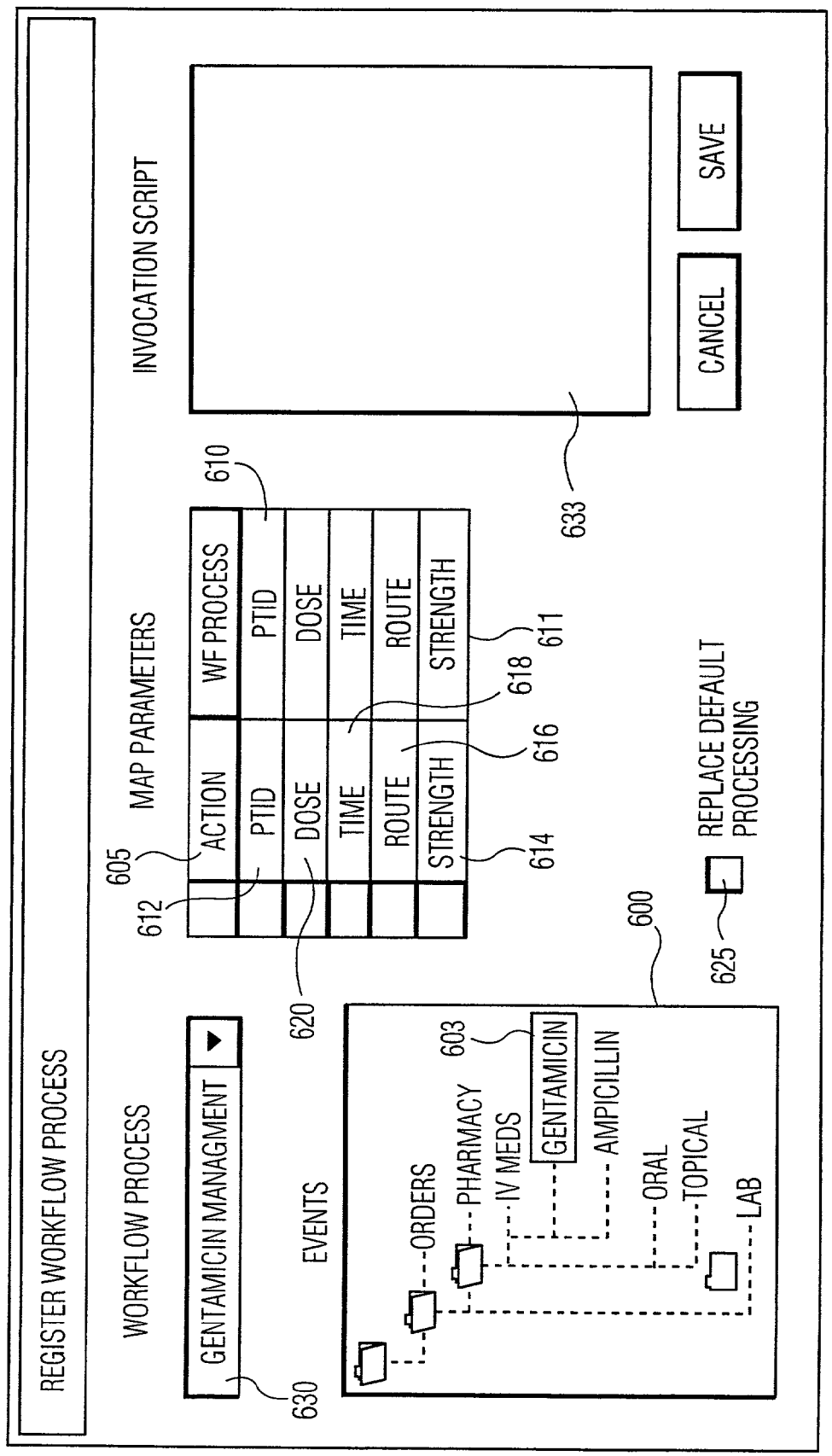
FIG. 3 shows a user interface display window for use indicating events and associated parameters that are usable in altering workflow processes comprising scheduled task sequences, according to invention principles.

FIG. 3 shows a user interface display window for use indicating events, associated parameters, executable procedures and other data that are usable in initiating or altering workflow processes comprising scheduled task sequences. The menu display image of FIG. 3 is derived by HIS 12 (FIG. 2) using an Extensible Markup Language (XML) document though in other embodiments the user interface of FIG. 3 may be derived based on other language files such as HTML, SGML etc. The FIG. 3 user interface includes prompt element 630 that presents a list of workflow processes available for selection. This enables a user to associate a workflow process such as Gentamicin Management selected via prompt element 630 with events such as a Gentamicin order 603 selected from hierarchically arranged events via prompt element 600. The user interface also enables a user to associate the selected workflow process (Gentamicin Management) with event parameters derived from HIS 12 (FIG. 2) and an executable procedure to be conveyed to the workflow process management routine upon occurrence of the selected event (here an order for Gentamicin). The event parameters from HIS 12 are mapped into corresponding parameters of the associated workflow process. The event parameters and executable procedure are selected for association with the selected workflow process via prompt elements 611 and 633 respectively. The FIG. 3 user interface enables an order with a parameter value associated with patient discharge to be used to initiate a patient discharge procedure, for example. As another example, a pharmacy order for Gentamicin IV may be used to initiate an aminoglycoside infusion process.

Particular event parameters such as the patient's identifier number (PTID) 612, dose (for example, 1 ml or 2 tablets) 620, time (for example, every 8 hours) 618, route (for example, intravenous) 616, and strength (for example, 80 mg/ml or 500 mg) 614 are selected via prompt element 611 which also indicates the corresponding identification label employed by the workflow process. The Gentamicin workflow process parameter label PTID 610 corresponds to the same label PTID 612 employed by HIS 12, for example. The workflow and HIS labels need not be the same in other cases and prompt element 611 advantageously presents to a user the parameter mapping of an HIS label to a corresponding workflow process label and enables a user to verify that the mapping is correct and to amend the mapping if required. Further, a user is able to select via selection item 625 whether a default workflow process is to be replaced by the event associated workflow process selected via prompt element 630. Selection of item 625 results in replacement of a scheduled default workflow process (or in another embodiment, particular identified tasks of the default workflow process) with the event associated workflow process selected via prompt element 630. Non-selection of item 625 results in the default workflow process being supplemented by the event associated workflow process. Such supplementing of a default workflow process may take the form of the event associated workflow process running entirely in addition to the default process or may comprise the addition of some task steps to the default process. Further, although not shown in the FIG. 3 user interface (to preserve drawing clarity), a user is able to select event parameter values for use as selection criteria for process initiation. For example, a workflow process can be registered for Ampicillin. Thereby a workflow process may be initiated if Ampicillin is ordered and can be configured to apply only if the administration route is intravenous. In addition, although not shown to preserve drawing clarity, the user interface of FIG. 3 may include an image element for prompting a user to select a default process that is to be modified or replaced and to associate this selected default process with an event associated workflow process. In another embodiment (and also not shown), the FIG. 3 user interface also allows a user to view the selected default process tasks and to select particular tasks to be modified by the event associated workflow process.

Figure 4:
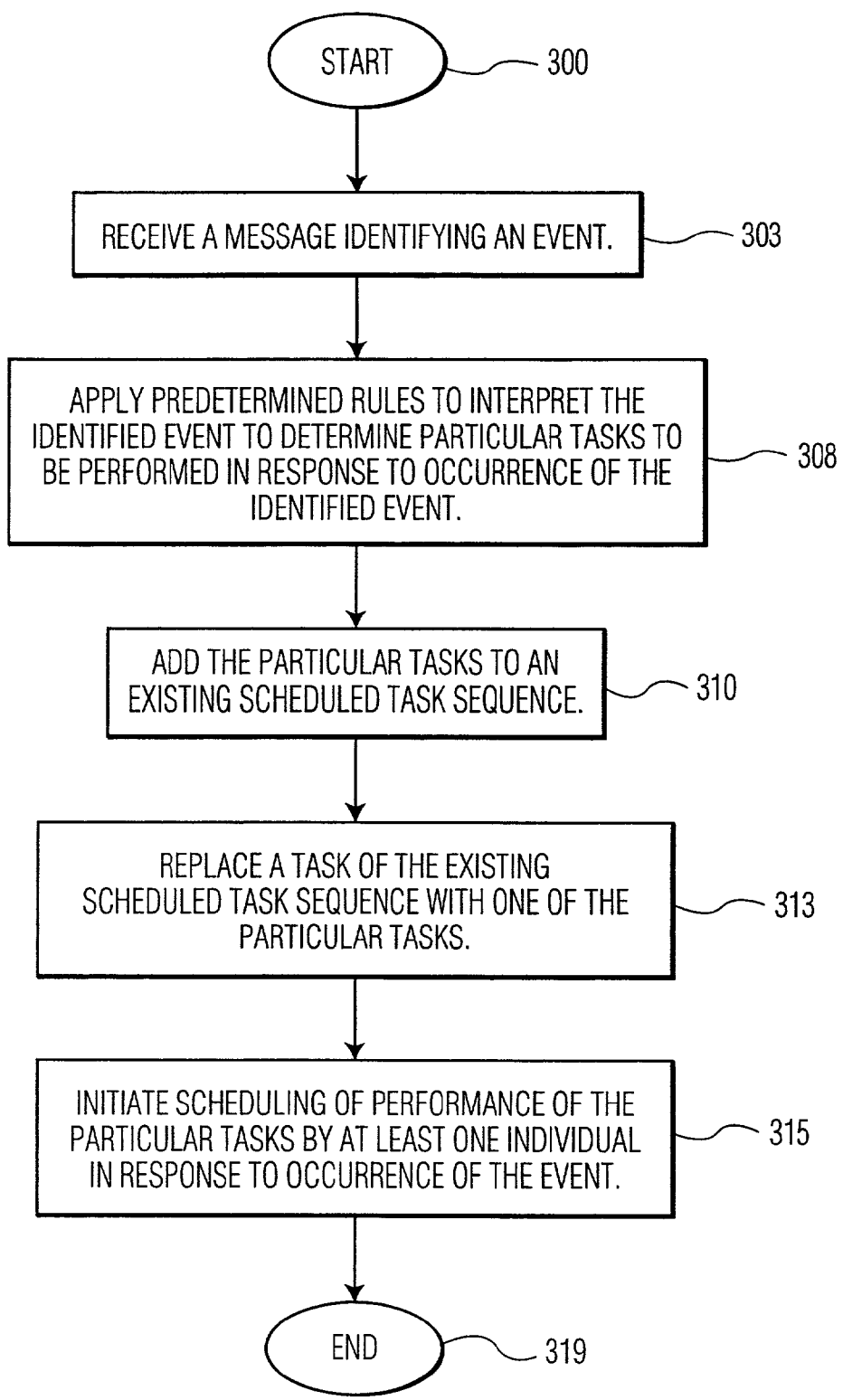
FIG. 4 shows a process flowchart for processing an event for use in replacing one or more tasks of a scheduled workflow process, according to invention principles.

FIG. 4 shows a process flowchart for use by event processor 28 (FIG. 2) for replacing one or more tasks of a scheduled workflow process with event associated tasks. In step 303 after the start at step 300, event processor 28 receives a message (e.g. from HIS 12 FIG. 2) identifying occurrence of an event. Processor 28 applies predetermined rules in step 308 to determine particular tasks to be performed in response to the identified event. Event processor 28 examines predetermined user selected information identifying those of the particular tasks that are to be added to an existing workflow process and those of the particular tasks that are to be substituted for existing tasks in the existing workflow process. The identified additional tasks are added to the existing workflow process in step 310 and the identified substitute tasks are substituted for the existing tasks in step 313. Further, the particular tasks are scheduled for performance as part of the existing workflow process by an entity such as an individual, group of individuals or personnel assigned to a role or another arrangement of personnel in step 315 and the process of FIG. 4 ends at step 319.

Figure 5:
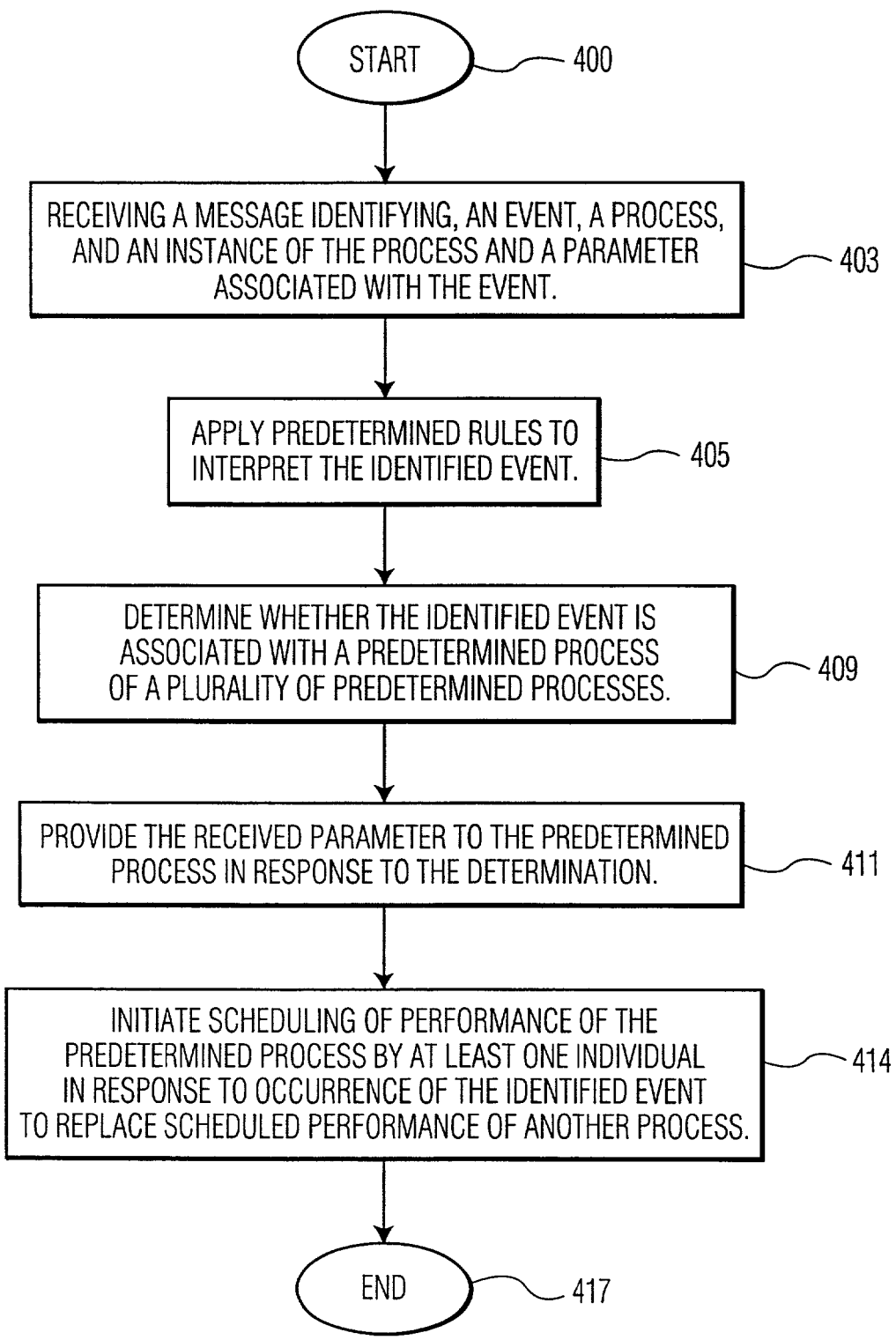
FIG. 5 shows a process flowchart for processing an event and associated parameters for use in replacing a scheduled workflow process, according to invention principles.

FIG. 5 shows a process flowchart for processing an event and associated parameters for use in replacing a scheduled workflow process with an event associated workflow process. In step 403 after the start at step 400 event processor 28 (FIG. 2) receives one or more messages (e.g. from HIS 12) identifying occurrence of an event as well as an associated parameter, process and instance of the process and also including a value of the event associated parameter. As previously explained an instance of a process is a copy of a workflow process and may comprise a particular use of the process for a specific patient, for example. Processor 28 applies predetermined rules in step 405 to interpret the identified event to select in step 409 a particular process (comprising predetermined tasks) from a plurality of predetermined processes. In step 411 processor 28 creates an instance of the selected predetermined process and provides this instance with the parameter values previously received in step 403. Processor 28 in step 414 schedules performance of the selected workflow process instance by an entity (e.g. at least one individual) to replace a scheduled workflow process. The process of FIG. 5 is complete at step 417.

As an example, the FIG. 2 system is considered in operation in conjunction with a configured IV antibiotic infusion workflow process. The user interface described in connection with FIG. 3 is employed to associate the antibiotic infusion workflow process with events comprising orders of a medication which have a drug type that is an antibiotic and a route that is Intravenous. This workflow process is designated to replace a default system process (e.g. following selection of icon 625 of FIG. 3). Therefore, in response to a physician placing an order for Gentamicin 120 mg IV for patient 1234, HIS 12 (FIG. 2) generates an event message indicating that Patient 1234 is the subject of a drug order for drug name "Gentamicin" specifically, drug type "aminoglycoside antibiotic", dose strength 120 mg, route IV. Event processor 28 receives the event message and determines that it has one or more subscribed predefined processes and that at least one of them is to replace the default system workflow process. Event processor 28 communicates a return message to HIS 12 to indicate that HIS 12 is not to proceed with the default workflow process but instead processor 28 is to implement a substitute a workflow process previously associated with the event via the FIG. 3 user interface. This return message is incorporated in the event acknowledgment message but in other embodiments multiple separate messages may be used. Event processor 28 maps data parameters received in the event message from HIS 12 to corresponding parameters required by the event associated substitute workflow process. In addition the event processor initiates creation and scheduling of processing of an instance of the substitute workflow process using rules engine 30 and workflow management system 36 (FIG. 2).

In a further example, the user interface described in connection with FIG. 3 is employed to associate an IV infusion workflow process with an "IV infusion failure" event for a particular patient identifier and a particular drug. Upon failure of a smart IV infusion pump to infuse the particular drug because of air in the line, the pump communicates an event message indicating "IV infusion failure" to event processor 28. The event message also includes pump identifier, patient identifier and drug parameter information derived from storage associated with the smart pump device. Event processor 28 determines that it has several workflow processes associated with the "IV infusion failure" event and accompanying particular received patient identifier and drug identifier. Thereupon, processor 28 initiates a call to the running instances of the event associated workflow processes with the particular received patient identifier and drug identifier using parameters derived from the IV infusion workflow process involving the "IV infusion failure" event. The notified workflow process modifies its behavior based upon the notification, and includes the scheduling of alerting a nurse to have the problem corrected.

Figure 6:
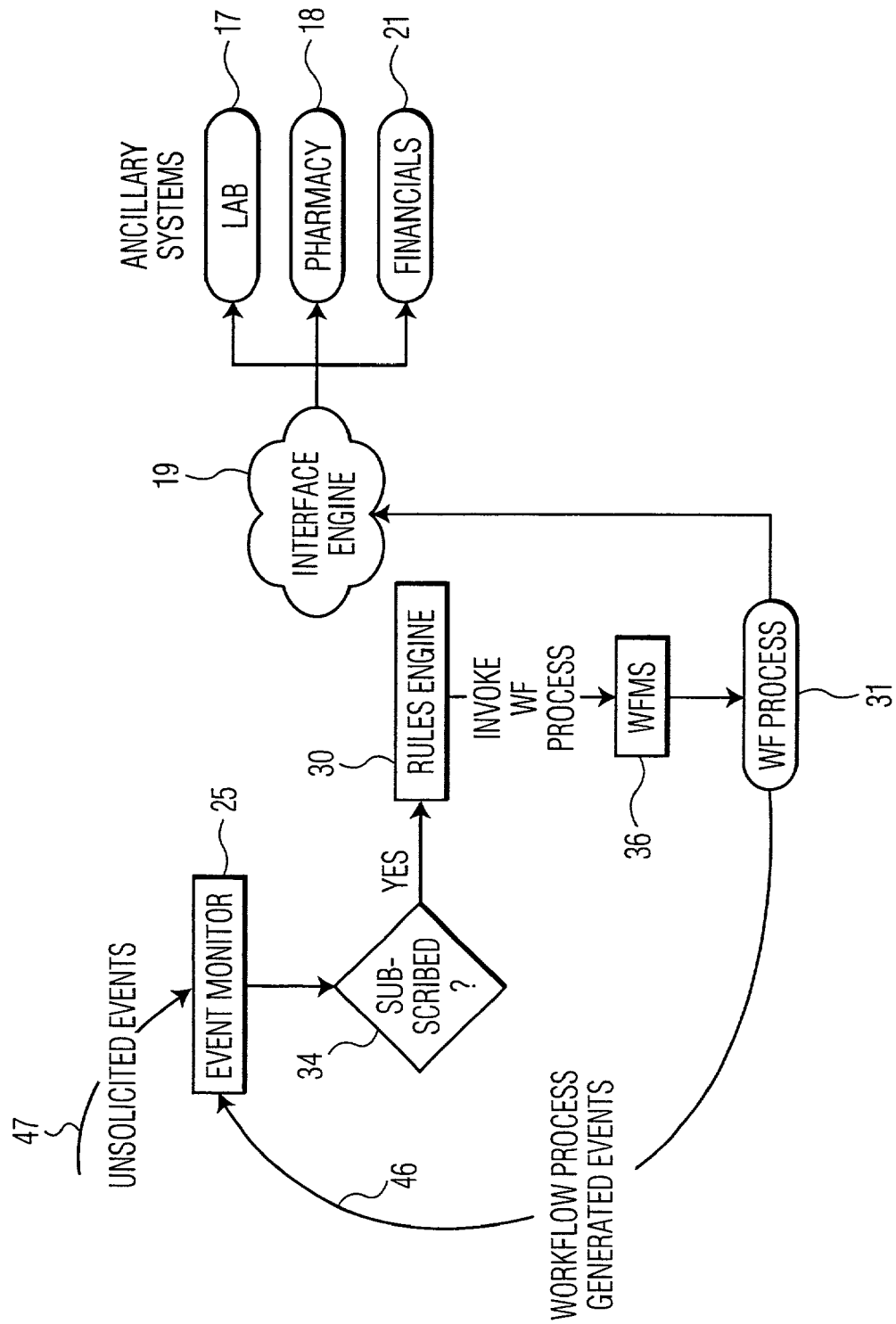
FIG. 6 shows a workflow and event management system responsive to events generated by other workflow processes and responsive to events external to an HIS, according to invention principles.

FIG. 6 shows a workflow and event management system responsive to events 46 generated by other workflow processes and responsive to events 47 external to an HIS. This provides enhanced capabilities for managing healthcare workflow. Thereby, for example, medication IV pumps, upon completion of infusion, may communicate an event message (including predetermined patient and medication identifiers stored by the pump) to event monitor 25. In response, event monitor 25 initiates an event associated workflow process that efficiently implements a predetermined healthcare regimen following infusion, and/or notifies running process instances of the occurrence of events for which they have registered interest. Similarly, patients may be provided with location or proximity detector badges enabling event messages to be generated upon a change in location of a patient and further promoting efficient care. In addition, in the FIG. 6 system, a first workflow process is configurable to generate an event message and communicate it to event monitor 25 for modifying a different second (or more) workflow process. Such an event message may include parameters identifying change in a patient location, patient status or nurse availability, for example.

The inventors have recognized that a problem arises in workflow management systems that constrain particular parameters or status indications to be exclusively associated with particular workflow process instances. Further that there is an advantage in employing global event associated parameters. Such a global event parameter may be associated with, and accessed by, more than one workflow process and process instance. This prevents the problem of having multiple workflow processes that interact potentially using a common event associated parameter with different incompatible values. Such a problem arises, for example, if a parameter indicating a location of a specific patient, set within a first running workflow process, is different to another location indication for the same patient maintained in a second process. This may occur for a variety of reasons such as if the patient location indication is updated at different intervals by the first and second processes or by use of a different location identification scheme by the first and second processes. The use of an individual global event parameter accessible from multiple running workflow processes prevents this problem. Thereby, a patient global event parameter indicating location (or other information item), stored at a single point, may be advantageously updated and accessed from multiple workflow processes based on a common patient identifier, for example.

In response to receiving an event message 46 or 47 and in similar fashion to the system of FIG. 2, event monitor 25 (FIG. 6) examines an internal map to determine whether a workflow process is associated with an event identified by an event identifier. If the identified event is associated with a particular workflow process (decision 34), it is determined whether the event associated workflow process is to be implemented. For this purpose event monitor 25 determines whether any received event parameter values or globally accessible event parameter values identified in the received event messages 46 or 47 are within an acceptable predetermined range. If the received parameters are acceptable and the event associated workflow process is to be implemented, event monitor 25 provides rules engine 30 with the event identifier and associated event parameter (including global parameter) values for use in implementing the particular workflow process. Rules engine 30 determines whether other event associated workflow process implementation pre-conditions are satisfied and support implementation of the event associated workflow process. Such pre-conditions include conditions derived from an executable procedure associated with the event associated workflow process, for example. The operation of the remainder of the FIG. 6 system is the same as for the system described in connection with FIG. 2. Specifically, rules engine 30 uses the information received from monitor 25 to call the Workflow Management System 36 and instruct it to implement the event associated particular workflow process 31. The implemented workflow process may also communicate with users and other systems (e.g. laboratory 17, pharmacy 18 and financial system 21) via interface engine 19.

Figure 7:
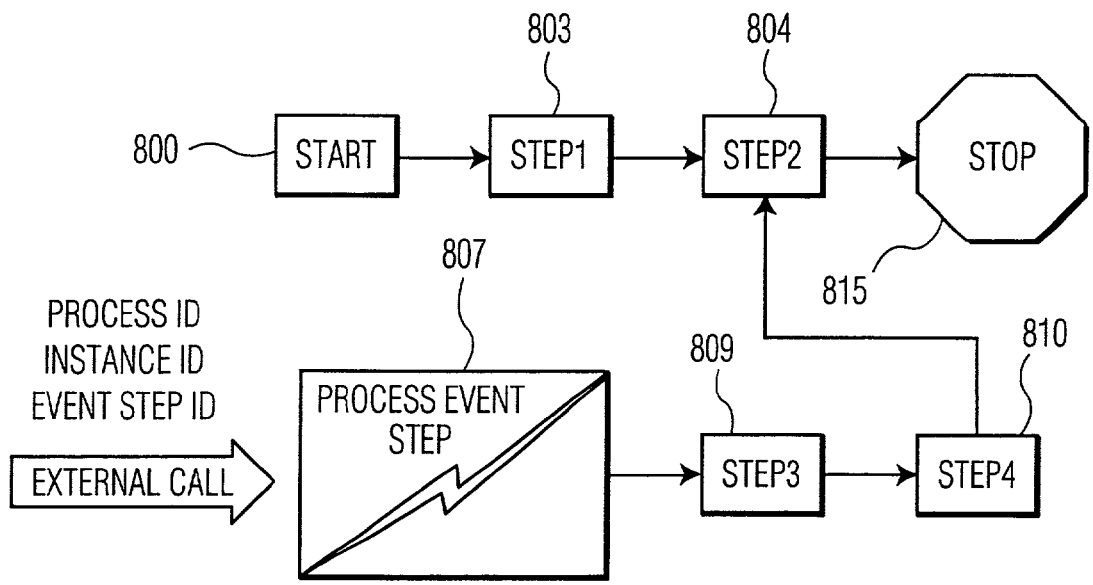
FIG. 7 shows a currently operating Healthcare Information System (HIS) workflow process responsive to a predetermined event generated by another workflow process.

FIG. 7 shows a currently operating Healthcare Information System (HIS) workflow process responsive to a predetermined event generated by another workflow process. It is known for workflow management systems to employ within a workflow process (comprising tasks 800-815) a special workflow task termed a "process event step" 807 that may be directly referenced and initiated within a currently operating workflow process. In order to initiate special event step 807, a calling application provides the workflow process with a process identifier, a specific process instance identifier and an event step identifier (e.g., identifying step 807). Further, such a process event step may be used to initiate a task sequence path (comprising tasks 807, 809, 810, 804 and 815) that is different to the normal workflow process task sequence path (comprising tasks 800, 803, 804 and 815). Thereby, providing a modified workflow process.

However, the inventors have recognized that existing workflow management systems are limited in the use of the process event step feature. This is because process instance identifiers are generated when copies (instances) of workflow processes are dynamically generated. They are not known in advance. Known systems typically require that in order to call such a process event step, the calling parameters (process identifier, a specific process instance identifier and an event step identifier) are predetermined and stored at the time they are associated with events generated from an HIS or other workflow processes. Consequently, subsequently dynamically created copies (instances) of a workflow process, including a process event step, have different unrecognized process instance identifiers. Therefore, such subsequently created process instances do not respond to event messages and are not initiated upon occurrence of an event associated with the original process. The system of FIG. 8 addresses this deficiency.

Figure 8:
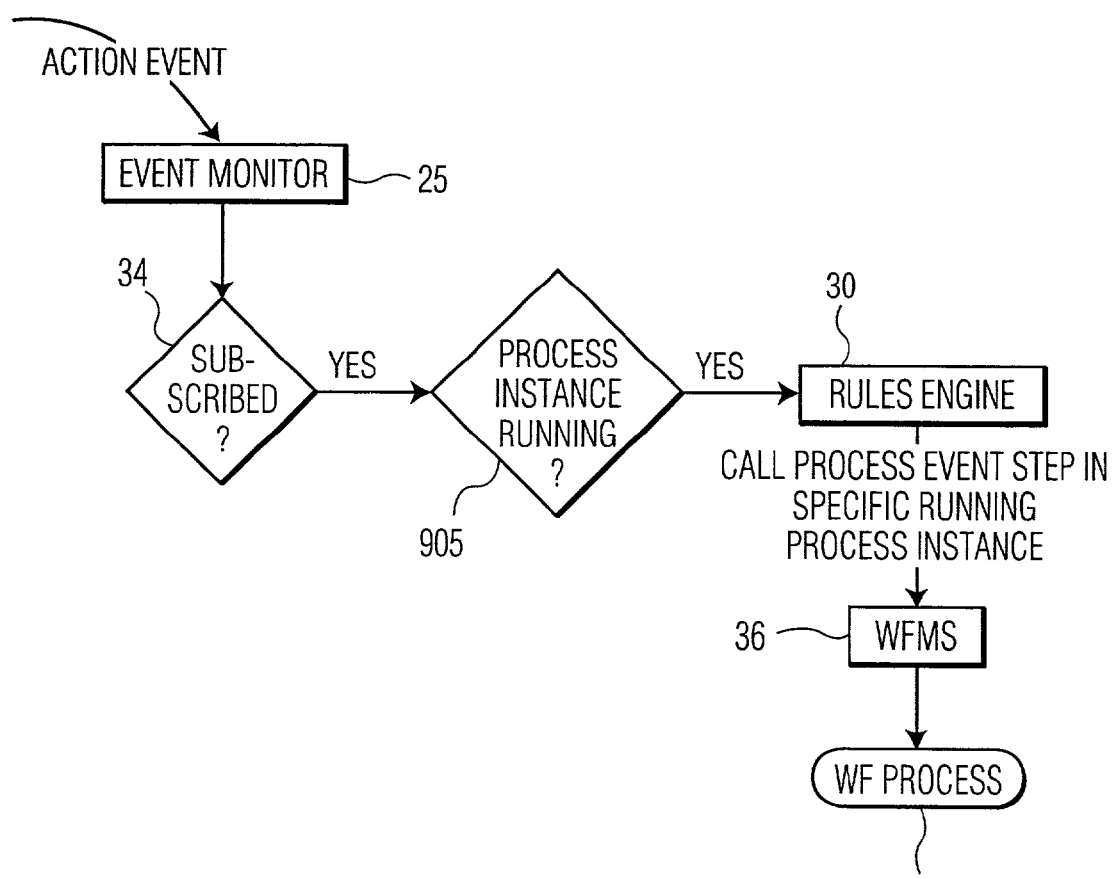
FIG. 8 shows a system for processing an event indication affecting a currently operating instance of a Healthcare Information System (HIS) workflow process, according to invention principles.

FIG. 8 shows a system for processing an event indication affecting a currently operating instance of a Healthcare Information System (HIS) workflow process. In the FIG. 8 system, upon initiation of an instance of workflow process 31 event monitor 25 is provided with its process identifier, its specific process instance identifier and its process event step identifier (or multiple process event step identifiers if they exist). Upon receiving an event message, event monitor 25 determines that the event identified by the received message is associated with workflow process 31 (decision 34). Further, event monitor 25 identifies any currently operating or scheduled instances of process 31 (decision 905). This is determinable since all instance identifiers of corresponding instances of process 31 have been provided to monitor 25 upon their initiation, or monitor 25 can query Workflow Management System 36 for this information when needed. Event monitor 25 also determines which of the identified currently operating instances of the identified event associated workflow process 31 are to be implemented based on criteria previously explained in connection with FIG. 2. Thereupon, event monitor 25 provides rules engine 30 with the event identifier and associated event parameter (including global parameter) values for use in implementing the particular workflow process 31 instances. Rules engine 30 uses the information received from monitor 25 to validate the process initiation and instruct Workflow Management System 36 to implement the event associated particular workflow process 31 instances.

As an example, if a dietary workflow process is associated with an event comprising a "nothing by mouth" order, event monitor 25 determines whether there is a running instance of the dietary workflow process for the same patient that is the subject of the "nothing by mouth" order. It does this using an internal database tracking operating process instances and associated process, instance and process event step identifiers as well as associated event parameters, executable procedures and other event related data. Event monitor 25 uses the identifiers in instructing rules engine 30 to call an appropriate process event step within the identified operating process instance. This event processing method provides a flexible, efficient and dynamically alterable workflow process management system. Using this system, workflow processes incorporating one or more process event steps may be devised that may be dynamically selected in response to an array of different events (internal and external to an HIS) occurring in a healthcare environment. For example, using multiple process event steps and such an event processing system an individual operating workflow process may comprise multiple different scheduled task sequences that are each selectable in response to occurrence of corresponding particular healthcare events. As a result operating workflow processes are dynamically modifiable in response to events occurring in the course of a patient treatment or diagnosis regimen. This contributes to providing an efficient flexible and responsive healthcare system.

The architectures and processes presented in FIGS. 1-8 are not exclusive. Other architectures and processes may also be derived in accordance with the principles of the invention to accomplish the same objectives. Further, the inventive principles may be advantageously employed in any workflow processing system responsive to events and is not limited to use in the healthcare field.

What is claimed is:

1. In a system for scheduling a set of tasks to be performed by at least one individual to support healthcare delivery, a method for providing a user interface for processing an event representing a change in circumstances potentially affecting healthcare delivered to a patient, comprising the steps of:
   in response to user command, initiating generation of at least one display image enabling a user in,
      identifying an event and an associated parameter;
      identifying a global parameter;
      designating a predetermined first process is associated with said event by associating identifiers with said event and said associated parameter, said predetermined process comprising a set of tasks to be performed by at least one individual to support healthcare delivery;
      designating a plurality of predetermined concurrently operable processes, including said first process, are associated with said global parameter for concurrently automatically sharing a value of said global parameter; and
      indicating a value of said associated parameter is to be provided to said first process in response to occurrence of said event;
   enabling access by said predetermined concurrently operable processes and sharing of said global parameter value;
   providing said associated parameter to said first process using a map in at least one repository associating event identifiers and parameter identifiers; and
   using said global parameter while executing said predetermined concurrently operable processes.

2. A method according to claim 1, including the step of filtering messages identifying events using said map to exclude messages conveying event identifiers unassociated with said predetermined first process from being passed to said process, wherein said at least one display image supports
   designating an executable procedure, for initiating a workflow process comprising a sequence of tasks to be performed by a worker or system, is associated with said event and wherein
   execution of said procedure is initiated in response to occurrence of said event.

3. A method according to claim 1, wherein said at least one display image supports
   designating a second process, comprising a scheduled sequence of tasks to be performed by at least one individual to support healthcare delivery, is associated with said event and
   determining said second process is to be at least one of, (a) replaced and (b) supplemented, by said predetermined first process in response to occurrence of said event.

4. A method according to claim 3, wherein said second process is supplemented by said predetermined first process by at least one of the steps of,
   (a) adding said tasks of said predetermined first process to tasks of said second process, and
   (b) substituting at least one of said tasks of said predetermined first process for a task of said second process.

5. A method according to claim 1, wherein said at least one display image supports
   designating a second process is to be at least one of, (a) replaced and (b) supplemented, by said predetermined first process in response to occurrence of said event, said second process comprising a scheduled sequence of tasks to be performed by at least one individual to support healthcare delivery and is different to said predetermined first process sequence of tasks.

6. A method according to claim 1, wherein said at least one display image supports
   designating predetermined parameter verification criteria is associated with said associated parameter.

7. A method according to claim 6, wherein
   said designated predetermined parameter verification criteria comprises at least one of, (a) a value range (b) a value type and (c) a parameter symbol check.

8. A method according to claim 1, wherein
   said plurality of predetermined concurrently operable processes comprise process instances.

9. A method according to claim 1, wherein said step of
   designating said predetermined first process is associated with said event comprises designating an instance of said predetermined first process is associated with said event.

10. A method according to claim 9, including the step of
    searching a database containing records indicating active processes to identify active process instances of said predetermined first process.

11. A method according to claim 1, including the step of
    in response to user command via said at least one display image, storing at least one of, (a) an event identifier identifying said event, (b) a process identifier identifying said predetermined first process and (c) an identifier identifying a particular instance of said predetermined first process.

12. A method according to claim 1, wherein
    scheduling said set of tasks includes a workflow engine integrated with a clinical information system and
    said event comprises at least one of, (a) an event resulting from action by healthcare personnel, (b) an event generated by an operating process, (c) an event generated by patient monitoring equipment and (d) an event generated by a medical device.

13. A method according to claim 1, wherein
    said display image indicates to a user a mapping of a first label representing said event associated parameter used by said predetermined first process to a corresponding second label representing said associated parameter used by a second process replaceable by said predetermined first process upon occurrence of said event.

14. A method according to claim 13, wherein
said first label is different from said second label.

15. A method according to claim 1, wherein
said at least one display image indicates individual tasks comprising said predetermined first process.

16. A method according to claim 15, wherein
said at least one display image supports user designation of a particular individual task of said individual tasks and said predetermined first process is initiated from said user designated particular individual task upon occurrence of said event.

17. A method according to claim 16, wherein
upon occurrence of said event, said predetermined first process omits at least one task prior to said designated particular individual task.

18. In a system for scheduling performance of a workflow, comprising a set of tasks, by at least one individual to support healthcare delivery, a method for providing a user interface for processing an event representing a change in circumstances potentially affecting healthcare delivered to a patient, comprising the steps of:

in response to user command, initiating generation of at least one display image enabling a user in, identifying first event and an associated global parameter, said associated global parameter being for use by multiple different process task sequences and stored at a location available for access by said multiple different process task sequences;

identifying a second event and an associated process specific parameter;

designating a predetermined first process is associated with said first event and second event by associating identifiers with said first event, second event and said associated global and process specific parameters, said predetermined first process comprising a set of tasks to be performed by at least one individual to support healthcare delivery; and designating said global and process specific parameter values are automatically to be provided to said first process in response to occurrence of said first event and said second event, respectively;

providing said global and process specific parameter values to said first process using a map in at least one repository associating event identifiers and parameter identifiers;

filtering messages identifying events using said map to exclude messages conveying event identifiers unassociated with said predetermined first process from being passed to said first process using said global parameter while executing said; and multiple different process task sequences.

19. A method according to claim 18, wherein said step of designating said predetermined first process is associated with said first event and second event includes the step of designating an instance of said predetermined first process is associated with said first event and second event.

20. A method according to claim 19, wherein
said particular instance of said predetermined first process comprises a particular use of said predetermined first process for a specific patient.

* * * * *